(12) United States Patent
Morgan et al.

(10) Patent No.: US 12,121,471 B2
(45) Date of Patent: Oct. 22, 2024

(54) ADJUSTMENT MEANS FOR A MANDIBULAR ADVANCEMENT DEVICE

(71) Applicant: BIOANALYTICS HOLDINGS LIMITED, Victoria (AU)

(72) Inventors: Owen Morgan, New South Wales (AU); Guoping Yan, Victoria (AU)

(73) Assignee: BIOANALYTICS HOLDINGS LIMITED, Victoria (AU)

( * ) Notice: Subject to any disclaimer, the term of this patent is extended or adjusted under 35 U.S.C. 154(b) by 263 days.

(21) Appl. No.: 17/638,679

(22) PCT Filed: Aug. 26, 2020

(86) PCT No.: PCT/AU2020/000088
§ 371 (c)(1),
(2) Date: Feb. 25, 2022

(87) PCT Pub. No.: WO2021/035278
PCT Pub. Date: Mar. 4, 2021

(65) Prior Publication Data
US 2022/0287869 A1    Sep. 15, 2022

(30) Foreign Application Priority Data

Aug. 26, 2019  (AU) ................................. 2019903107

(51) Int. Cl.
*A61F 5/56* (2006.01)
*A61C 7/06* (2006.01)

(52) U.S. Cl.
CPC ................ *A61F 5/566* (2013.01); *A61C 7/06* (2013.01)

(58) Field of Classification Search
CPC ...... A61F 5/566; A61F 5/56; A61F 2005/563; A61F 5/05891; A61C 7/06; A61C 7/36; A61C 7/00; A61C 7/10; A61C 19/045

(Continued)

(56) References Cited

U.S. PATENT DOCUMENTS

| | | |
|---|---|---|
| 5,810,013 A | 9/1998 | Belfer |
| 2007/0209666 A1 | 9/2007 | Halstrom et al. |

(Continued)

FOREIGN PATENT DOCUMENTS

| | | |
|---|---|---|
| WO | WO 2006/072147 A1 | 7/2006 |
| WO | WO 2011005299 A2 | 1/2011 |

(Continued)

OTHER PUBLICATIONS

European Search Report in EP 20859037.2, dated Apr. 5, 2023 (7 pages).

*Primary Examiner* — Victoria Hicks Fisher
(74) *Attorney, Agent, or Firm* — Bookoff McAndrews, PLLC

(57) ABSTRACT

The present invention is an adjustment means for a mandibular advancement device, having both intraoral and extraoral portions, including a body portion at the interface. The extraoral portion includes a lower arm and a curved upper arm. The posterior end of the upper arm includes a pad assembly that is adapted to make contact with and apply pressure to the subnasal maxillary bone. The lower arm includes a thread that is adapted to be threaded into an adjustment wheel so that turning in one direction causes the extraoral portion to retract into the body portion, causing the upper pad to apply greater pressure to the subnasal maxillary bone. Turning the adjustment wheel in the opposite direction causes the upper pad to apply decreased pressure. One complete revolution of the adjustment wheel in a first or second direction causes the extraoral portion to extend or retract by one millimetre in length.

7 Claims, 5 Drawing Sheets

(58) Field of Classification Search
USPC .......................................................... 128/848
See application file for complete search history.

(56) References Cited

U.S. PATENT DOCUMENTS

| | | |
|---|---|---|
| 2011/0168188 A1 | 7/2011 | Moore et al. |
| 2011/0217674 A1 | 9/2011 | Hanewinkel et al. |
| 2014/0224257 A1 | 8/2014 | Abramson |

FOREIGN PATENT DOCUMENTS

| | | |
|---|---|---|
| WO | WO 2019/071291 A1 | 4/2019 |
| WO | WO 2019/094744 A1 | 5/2019 |

ADJUSTMENT MEANS FOR A MANDIBULAR ADVANCEMENT DEVICE

CROSS-REFERENCE TO RELATED APPLICATIONS

This application is the U.S. national phase entry under 35 U.S.C. § 371 of International Application No. PCT/AU2020/000088, filed on Aug. 26, 2020, which claims the benefit of priority of Australian Patent Application No. 2019903107, filed on Aug. 26, 2019.

FIELD OF THE INVENTION

This invention relates to mandibular advancement devices, particularly to devices worn by a person to prevent obstructive sleep apnoea, and in particular to adjustment means for the extraoral portion of that device.

BACKGROUND OF THE INVENTION

A mandibular advancement device of the type referred to in this specification is already disclosed in WO 2019/071291 A1 and WO 2006/072147. The mandibular advancement device disclosed has both intraoral and extraoral portions. The present invention is mainly concerned with the extraoral portion of the device.

The extraoral portion of the device is substantially J-Curved and initially extends directly away from the face of the wearer, then curves back towards the face. The posterior end of the J curve includes an upper pad that contacts the subnasal maxillary bone. The parts of the intraoral portion that make contact with the mandible are braced against the contact of the upper pad. By increasing or decreasing the pressure on the upper pad, the position of the mandible is changed.

One of the main problems surrounding this arrangement is that often manual adjustments need to be made while the device is worn. Typically, this happens during the night as the wearer is in bed. As disclosed in the previous specification listed above, a screw type arrangement has been made that moves the extraoral portion inwardly or outwardly. However, due to the fact that this typically happens in a bedroom at night while people are sleeping, it is often difficult in the dark, and also because the adjustment happens typically out of sight of the user due to the position of the adjustment means, to determine exactly how far the extraoral portion has been moved.

Further to this, when a person gets a new device as either a replacement, or as an ancillary device, there is no easy way to pre-set the device to a first position that the wearer knows will best suit his or her particular physiology.

It is therefore an object of the present invention to provide adjustment means for the extraoral portion of a mandibular advancement device that at least mitigates some of the aforementioned problems.

DISCLOSURE OF THE INVENTION

Accordingly, in one form, the present invention is an adjustment means for a mandibular advancement device. The mandibular advancement device being of the type having both intraoral and extraoral portions, including a body portion that is at the interface between the intraoral and extraoral portions and thereby is part intraoral and part extraoral. The extraoral portion includes a lower arm that is substantially straight and extends directly outwardly from the extraoral part of the body portion, and a curved upper arm that curves upwardly from the lower arm and back towards the face of a person using the device. The posterior end of the upper arm includes a pad assembly that is adapted to make contact with and apply pressure to the subnasal maxillary bone of the wearer. A substantial portion of the lower arm includes a thread that is adapted to be threaded into an adjustment wheel that is housed within the extraoral part of the body portion so that turning the adjustment wheel in one direction causes the extraoral portion to retract into the body portion, and thereby cause the upper pad to apply greater pressure to the subnasal maxillary bone, and turning the adjustment wheel in the opposite direction causes the extraoral portion to extend out from the extraoral part of the body portion, thereby causing the upper pad to apply decreased pressure to the subnasal maxillary bone. The threaded portions in both the lower arm and the adjustment wheel are arranged so that one complete revolution of the adjustment wheel causes the extraoral portion to extend or retract by one millimetre in length, and the changes in pressure on the subnasal maxillary bone combine with the intraoral portion of the device to adjust the position of the mandibular of the wearer of the device.

Preferably, the device includes haptic feedback at regular distance increments to a person manipulating the adjustment wheel.

Preferably, the haptic feedback is felt upon each complete revolution of the adjustment wheel, either clockwise or counter-clockwise.

In another preferred form of the invention, the device includes an audible click noise that is heard at regular distance increments by a person manipulating the adjustment wheel.

Preferably, the audible click noise is heard at each complete revolution of the adjustment wheel, either clockwise or counter-clockwise.

In another preferred form of the present invention, the adjustment wheel includes means that are adapted to engage with corresponding means on the body portion so that as the adjustment wheel makes any complete 360° revolution, the corresponding pair of at least one small lateral projections interfere with each other thereby creating a haptic sensation and/or an audible click.

Preferably, the adjustment wheel includes a small groove that is adapted to engage with a corresponding small lateral projection on the body portion so that as the adjustment wheel makes any complete 360° revolution, the small lateral projection is adapted to interfere with the groove thereby creating a haptic feedback and/or an audible click.

In another preferred form of the present invention, the adjustment wheel includes at least one small lateral projection that is adapted to impinge upon a corresponding at least one small lateral projection on the body portion so that as the adjustment wheel makes any complete 360° revolution, the corresponding pair of at least one small lateral projections interfere with each other thereby creating a haptic feedback and/or an audible click.

Preferably, a substantial portion of the lower arm includes measurement graduations that enable a person to have visual means to initially adjust to position of the extraoral portion prior to having the device used by using the adjustment wheel.

DETAILED DESCRIPTION OF THE PREFERRED EMBODIMENTS

Figure 1:
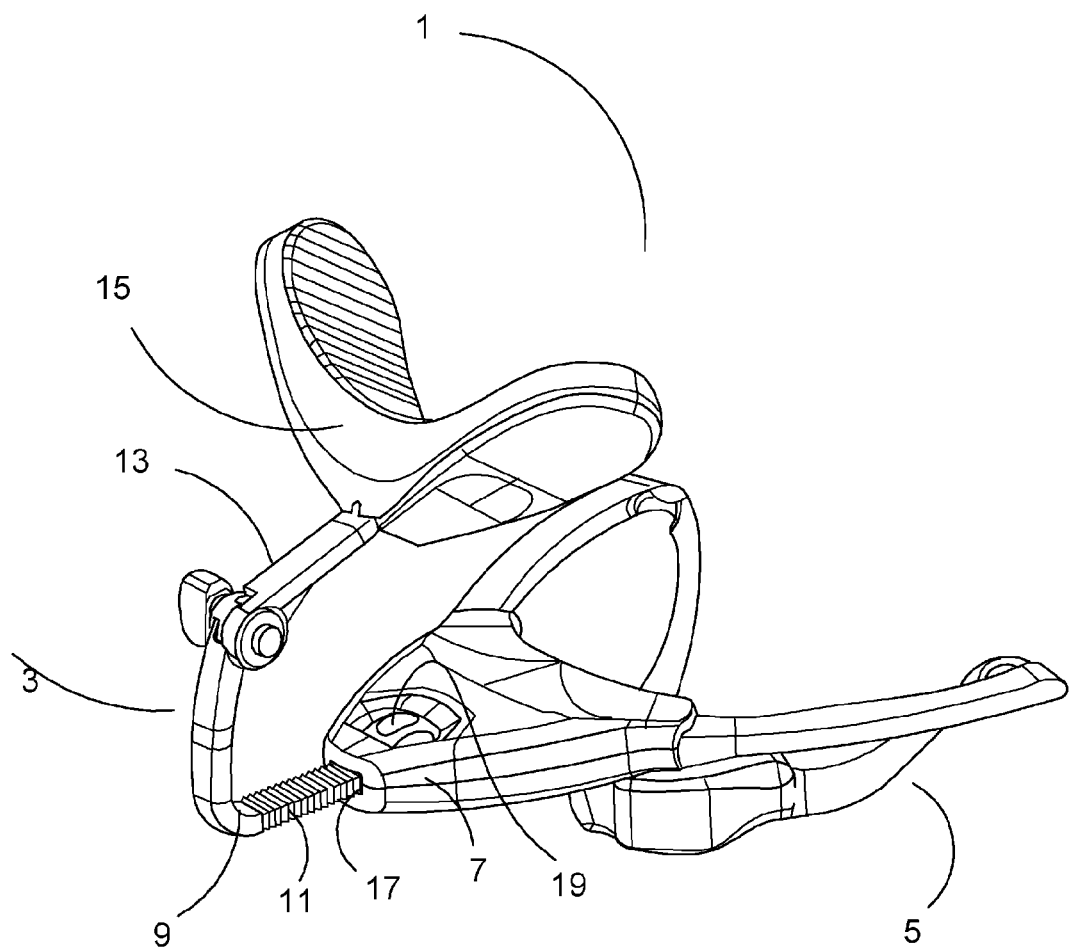
FIG. 1 is an isometric view of the mandibular advancement device.

Turning firstly to FIG. 1, where we are shown the mandibular advancement device 1. In this isometric view, we can see the extraoral portion 3, the intraoral portion 5 and the body portion 7 that is intraoral in the posterior part and extraoral in the anterior part. In the view, we can see that the lower arm 9 is substantially straight and emerges directly forward out of the body portion 7. The lower arm 9 includes a thread 11 that extends substantially along its length. The extraoral portion 3 also includes a curved upper arm 13 that curves upwardly from the anterior end of the lower arm, and back towards the face of the wearer. At the posterior end of the upper arm 13 there is pad assembly 15 that is adapted to make contact with, and apply pressure to, the subnasal maxillary bone of the wearer. This is best illustrated in FIG. 2b. As shown, the posterior portion of the lower arm 9 is adapted to slide inside an anterior cavity 17 in the body portion 7. The body portion 7 includes an adjustment wheel 19 that has an aperture that is adapted to receive the lower arm 9 within. The aperture is internally threaded. The internal thread of the adjustment wheel 19 is adapted to engage with the externally threaded portion of the lower arm. The threads are arranged so that one full 360° turn of the adjustment wheel causes the lower arm to move a distance of one millimetre. Rotation of the adjustment wheel 19 in one direction causes the lower arm 9 to retract into the body portion 7, and rotation of the adjustment wheel 19 in the opposite direction causes the lower arm 9 to extend further out from the body portion. These movements of the lower arm 11 either cause the pad assembly to exert more or less pressure on the subnasal maxillary bone of the wearer. The pressure of the pad assembly 15 on the subnasal maxillary bone couples with the intraoral portion of the mandibular advancement device to force the mandibular into a new position.

Figure 2:
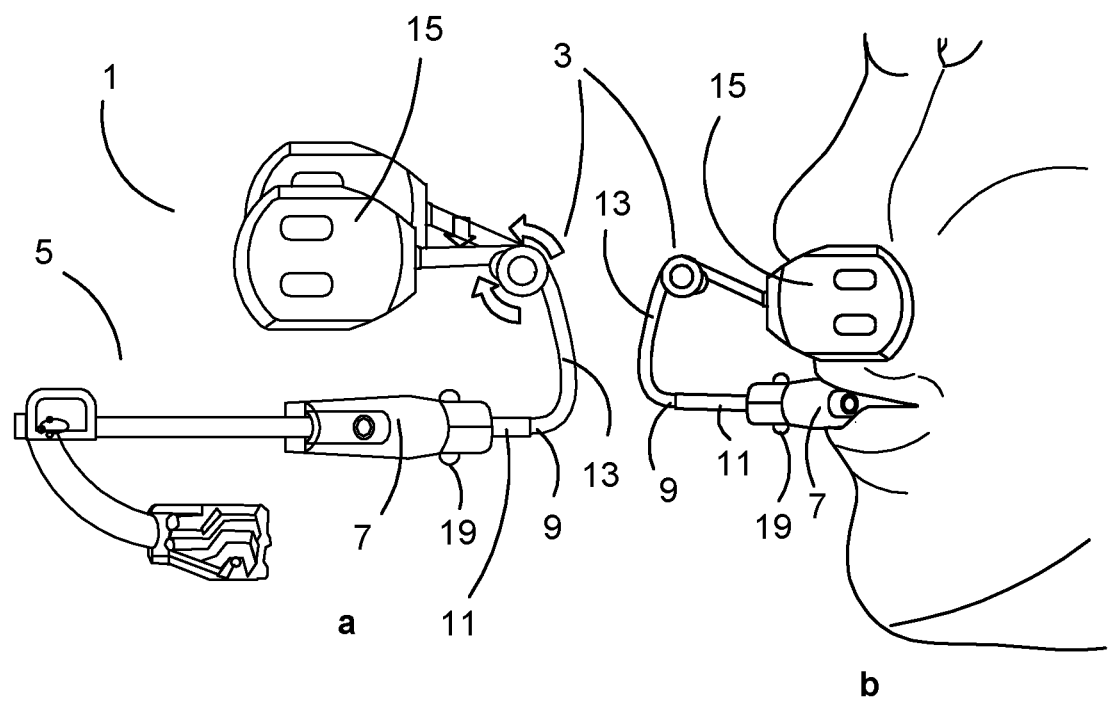
FIG. 2a is a side view of the mandibular advancement device.
FIG. 2b is a side view of the mandibular advancement device being worn by a wearer.

Now turning to FIG. 2a, we are shown a side view of the mandibular advancement device 1. In this view it is easier to see the intraoral and extraoral portions of the device. FIG. 2 shows the device 1 in use. In this view we can see the anterior portion of the body portion 7 extending from the wearer's mouth. The pad assembly 15 is arranged to make contact with the subnasal maxillary bone. Rotational adjustment of the adjustment wheel 19 causes the pad assembly 15 to exert more or less pressure on the subnasal maxillary bone, and this combines with the intraoral portion of the device 1 to enable manual adjustment of the position of the mandibular.

Figure 3:
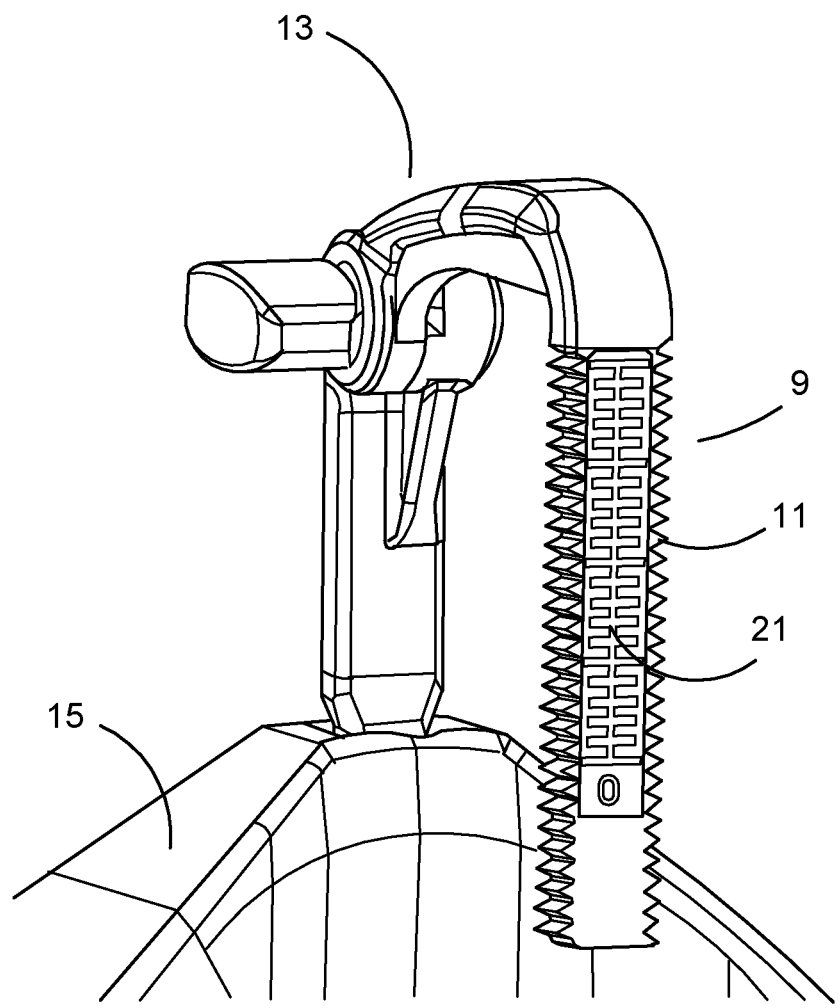
FIG. 3 shows an isometric view from below of part of the extraoral portion of the mandibular advancement device.
Figure 4:
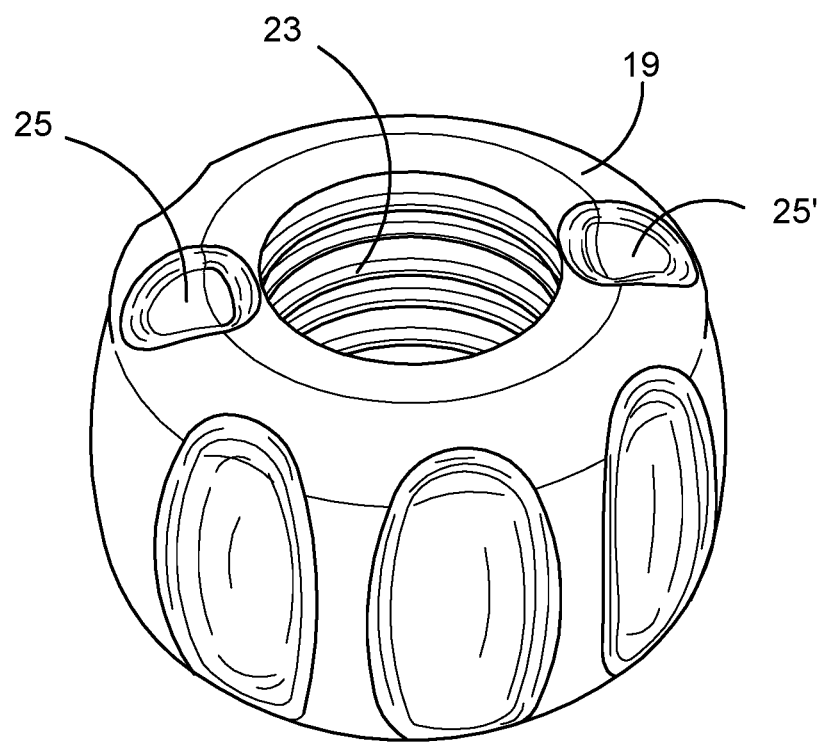
FIG. 4 shows a preferred form of the adjustment wheel.

Turning to FIG. 3, we are shown a close-up isometric view of the underside of most of the extraoral portion of the device. In this view, we can see further detail of the lower arm 9, the threaded portion 11, the upper arm 13 and the pad assembly 15. Preferably, the lower arm 9 includes graduated distance indicators 21. These assist a person setting up a device for first use. The user can adjust the lower arm into a general position by using the adjustment wheel 19 to move the lower arm 9 into a rough first position, by using the graduated distance indicators 11 as a guide, and then when the device is inserted into the wearer's mouth, fine adjustments of the lower arm's position can be made in order to maximise the effect of the device and the wearer's comfort.

Figure 5:
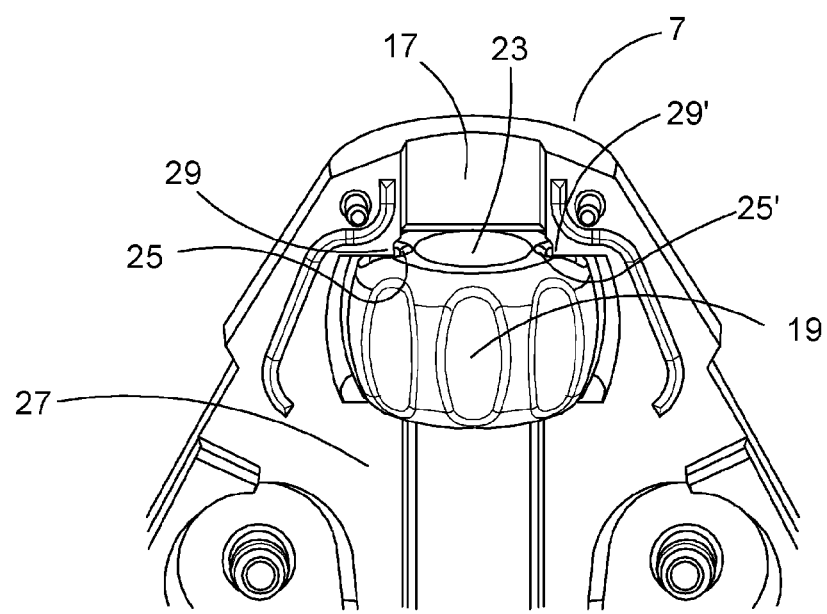
FIG. 5 shows the bottom half of the body portion of the mandibular advancement device with the adjustment wheel in place.

Preferably, as shown in FIG. 5, the adjustment wheel 19 has an internal thread 23 that engages with the external thread on the lower arm 9. The wheel has at least one groove 25, but in this example, two diametrically opposed grooves 25 and 25' respectively are shown.

In a preferred embodiment, the body portion 7 is made up of both a top and bottom plate. In this illustration, only the bottom plate 27 is shown. In this view, it is easy to see the cavity 17 formed into the anterior end of the body portion 7 of the device. The anterior portion of the lower arm 9 is adapted to be insertable into the cavity 17 and into the adjustment wheel 19. The external thread 11 of the lower arm 9 is adapted to engage with the internal thread 23 of the adjustment wheel 19. In this view, there is a pair of small projection 29 and 29' that are adapted to engage with the grooves 25 and 25' of the adjustment wheel 19 so that when adjustment wheel 19 is rotated, at a fixed amount of turn, the engagement of the projection 29 and 29' causes at least haptic feedback to the person adjusting the position of the lower arm 9. In a preferred embodiment, the engagement of the small projection 29 and 29' also causes an audible click. The interengagement of the threads as the adjustment wheel 19 is turned is arranged so that one full rotation of the wheel 19 causes the lower arm 9 to move a distance of 1 millimetre. In this example, because there are two grooves 25 and 25' included on the wheel 19, then the haptic and audible feedback will occur on every half full turn of the wheel 19.

While the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

The reference to any prior art in this specification is not, and should not be taken as, an acknowledgment or any form of suggestion that such prior art forms part of the common general knowledge.

The invention claimed is:

1. A mandibular advancement device having both intraoral and extraoral portions, including a body portion that is at an interface between the intraoral and extraoral portions and thereby includes an intraoral part and an extraoral part, and wherein the extraoral portion includes a lower arm that is substantially straight and extends directly outwardly from the extraoral part of the body portion, and a curved upper arm that curves upwardly from the lower arm and back towards the face of a person using the mandibular advancement device, and wherein a posterior end of the upper arm includes a pad assembly that is adapted to make contact with, and apply pressure to, the subnasal maxillary bone of the person, and wherein a substantial portion of the lower arm includes an external thread that is adapted to be threaded into an internal thread on an adjustment wheel that is housed within the extraoral part of the body portion so that turning the adjustment wheel in a first direction causes the extraoral portion to retract into the body portion, and thereby cause the pad assembly to apply greater pressure to the subnasal maxillary bone, and turning the adjustment wheel in a second direction, wherein the second direction is opposite to the first direction, causes the extraoral portion to extend out from the extraoral part of the body portion, thereby causing the pad assembly to apply decreased pressure to the subnasal maxillary bone, and wherein the external thread on the lower arm and the internal thread on the adjustment wheel are arranged so that one complete revolution of the adjustment wheel in the second direction causes the extraoral portion to extend by one millimeter in length, and one complete revolution in the first direction causes the extraoral portion to retract by one millimeter in length, and wherein changes in pressure on the subnasal maxillary bone caused by an extension or retraction of the extraoral portion combine with the intraoral portion of the mandibular advancement device to adjust a position of the mandible of the person wearing the mandibular advancement device.

2. The mandibular advancement device as defined in claim 1 wherein the mandibular advancement device includes haptic feedback at regular distance increments to a person manipulating the adjustment wheel.

3. The mandibular advancement device as defined in claim 2 wherein the mandibular advancement device produces a haptic feedback upon each complete revolution of the adjustment wheel, either clockwise or counter-clockwise.

4. The mandibular advancement device as defined in claim 2 wherein the mandibular advancement device produces an audible click noise at regular distance increments by a person manipulating the adjustment wheel.

5. The mandibular advancement device as defined in claim 4 wherein the mandibular advancement device produces an audible click noise at each complete revolution of the adjustment wheel, either clockwise or counter-clockwise.

6. The mandibular advancement device as defined in claim 3 wherein the adjustment wheel includes a small groove that is adapted to engage with a corresponding small lateral projection on the body portion so that as the adjustment wheel makes any complete 360° revolution, the small lateral projection is adapted to interfere with the small groove thereby creating a haptic feedback and/or an audible click.

7. The mandibular advancement device as defined in claim 1 wherein a substantial portion of the lower arm includes measurement graduations that enable a person to have visual means to initially adjust the position of the extraoral portion prior to using the mandibular advancement device so that an initial position of the lower arm is able to be preset prior to the person using the mandibular advancement device.

* * * * *